(12) United States Patent
Barr

(10) Patent No.: US 6,368,579 B1
(45) Date of Patent: Apr. 9, 2002

(54) OAT PROTEIN COMPLEX SUNBLOCK AND METHOD OF USE

(75) Inventor: Teresa Leigh Barr, 1730 Landes St., Port Townsend, WA (US) 98368

(73) Assignee: Teresa Leigh Barr, Port Townsend, WA (US)

( * ) Notice: Subject to any disclaimer, the term of this patent is extended or adjusted under 35 U.S.C. 154(b) by 0 days.

(21) Appl. No.: 09/921,164

(22) Filed: Aug. 2, 2001

Related U.S. Application Data

(60) Provisional application No. 60/223,776, filed on Aug. 8, 2000.

(51) Int. Cl.⁷ .............................. A61K 7/42; A61K 7/44; A61K 7/00; A61K 35/78
(52) U.S. Cl. .......................... 424/59; 424/60; 424/400; 424/401; 424/725.1; 424/750
(58) Field of Search .......................... 424/59, 60, 400, 424/401, 725.1, 750

(56) References Cited

U.S. PATENT DOCUMENTS

| | | | | |
|---|---|---|---|---|
| 5,573,785 A | * | 11/1996 | Murphy et al. | 424/59 |
| 5,653,967 A | * | 8/1997 | Murphy et al. | 424/70.1 |
| 6,153,208 A | * | 11/2000 | McAtee et al. | 424/402 |
| 6,193,956 B1 | * | 2/2001 | Lin et al. | 424/45 |

* cited by examiner

*Primary Examiner*—Shelley A. Dodson
(74) *Attorney, Agent, or Firm*—Buskop Law Group, P.C.; Wendy K. Buskop

(57) ABSTRACT

A composition containing enhanced colloidal oatmeal which utilizes other avena sativa ingredients to neutralize the discomfort, irritation and inflammation of the skin, as well as maintaining normal skin, and can be used to treat many types of discomforts, including itching; due to poison ivy, oak and sumac, insect bites, sunburn, chicken pox, hives, prickly heat, chafing, and the like while maintaining the normal pH of the skin.

6 Claims, No Drawings

OAT PROTEIN COMPLEX SUNBLOCK AND METHOD OF USE

The present application claims priority to Provisional Patent Application Serial No. 60/223,776 filed in the U.S. Patent and Trademark Office on Aug. 8, 2000.

BACKGROUND OF THE INVENTION

In one aspect, this invention relates to a position of matter useful for treating skin discomforts as well as maintaining normal skin. In another aspect, this invention relates to a method for treating skin discomforts as well as, maintaining normal skin. In yet another aspect, this invention relates to formulating a reliever of skin discomforts as well as normal skin care maintenance.

Oatmeal has been used throughout history as a topical application for skin, in cosmetic preparations, raw and for the bath. It has been used ground dry as well as cooked. Technology now allows use to extract certain properties from the entire oat, not just the grain. Colloidal Oatmeal, a product processed by grinding of the oat grain, has been consistently recommended for adults, geriatrics as well as infants in lotions, creams, shampoos, conditioners, soaps, ointments and the like as well as in bath and cleansing products, and poultices. Colloidal oatmeal additions to skin have a soothing effect on inflammation and irritation, as well as being an effective cleanser or topical powder. Oat Protein is actively substantive to hair and skin contributing to conditioning.

Several topical agents (creams, ointments, liniments and the like), as well as shampoos, conditioners and bath products have been utilized for the relief of treating skin discomforts as well as maintaining normal skin. Most of these have provided a little, but only temporary, relief to persons suffering treating skin discomforts and maintaining normal skin. Many combinations of varying ointments, creams, aqueous solutions, liniments, shampoos, conditioners, bath products and the like for the treatment of treating skin discomforts as well as maintaining normal skin are known. The most efficacious of these contains as its active ingredient the flour product derived from the grain of the avena sativa plant, commonly known as oats. Oat derived colloidal oatmeal is devised for external application to the affected area of the body by applying directly to the desired area for treating skin discomforts as well as maintaining normal skin. The active ingredient is colloidal oatmeal.

The Federal Register, Volume 54 Number 190, Tuesday, Oct. 3, 1989, Proposed rules states:

Agency's Tentative Conclusions on the Comments (Exerts as follows):

The Panel found colloidal oatmeal at all concentrations to be safe an effective as a bath additive, cleansing bar, and soak for symptomatic relief and treatment of dry skin and the resulting itching.

The comment contended that colloidal falls within the topical analgesic panel's definition of a skin protectant. The comment argued that, due to its physical and chemical properties, colloidal oatmeal isolates exposed skin or mucous membrane surface from harmful or annoying stimuli. (See proposed 347.3 at 43 FR 34628 at 34648; Aug. 4, 1978.) The comment also stated that colloidal oatmeal that is dispersed in water and applied to the skin and leaves behind an occlusive film barrier that is helpful in protecting skin against irritation and in soothing irritated or pruritic skin conditions. The comment added that colloidal oatmeal when added to water control osmotic pressure of water with respect to the skin and permits adequate water to enter into the stratum corneum. The comment stated that oatmeal leaves behind a thin occlusive film on the skin and this serves to hold in the adsorbed water. The result of this coating is that the skin is protected against irritation and hence the ingredient has an antipruritic and generally soothing effect. The comment noted that the topical analgesic panel stated that 43 FR 34830 that ". . . the fluids from seeping rashes or toxic dermatoses (poison ivy, poison sumac, poison oak, etc.,) are absorbed or adsorbed by many of these drugs. Often itching is ameliorated." Based on the above comment contended that the following claim for colloidal oatmeal is justified. "For prompt, temporary relief of itchy, sore, sensitive skin due to . . . poison ivy and oak . . .".

The topical analgesic panel stated at 43 FR 34630 that well controlled clinical studies have been conducted for most of the skin protectant ingredients. The Panel recommended that the requirement for well controlled studies be waived on the grounds that clinical studies are not necessary to support the use of mechanical barriers such as these ingredients to protect the skin form further injury. The agency agrees with this recommendation regarding skin protectant (physical barrier) type ingredients. In addition, the agency agrees that colloidal oatmeal qualifies as a skin protectant because of its barrier like qualities. Montebovi (Ref 2) identified and evaluated a number of hydrophilic colloids including colloidal oatmeal using the Gold Number is an in vitro physical chemical determination intended to measure the protective ability of hydrophilic colloids.

With initial as well as persistent application, colloidal oatmeal is effective to relieve and treat skin discomforts and maintaining normal skin, such as, diaper rash, prickly heat, poison oak, ivy and sumac, reduces sunburn discomfort, hives and insect bites, eczema and psoriasis, chicken pox, as well as its non detergent or surfactant free cleansing abilities.

Colloidal oatmeal is also effective to relieve the various itching, burn relief, itching and inflammation caused from shingles, itching and inflammation caused by miscellaneous sources such as medication reactions, diaper rash, insect bites, sunburn, adhesive bandage irritation and the like. It is further commonly prescribed to reduce the irritation of eczema and psoriasis, and "phantom itching", as from medication, or no known source, and the like.

Unfortunately, although colloidal oatmeal is often the most effective agent available, the beneficial ingredients, oat beta-glucan, active oat extract and oat protein has been degraded or even lost during the refining and separation process.

The loss of these essential proteins and nutrients through refinement has limited the properties of colloidal oatmeal, and does not use its full potential to help promote healing and to treat skin irritations and other types of skin complaints caused by numerous stimuli, such as melanoma and damage caused by radiation, chemotherapy as well as deep tissue burning, as well as itching caused by medication, and also to maintain normal skin.

A colloidal oatmeal based raw material which contains all the beneficial proteins, active oat extracts, and oat beta-glucan, would be extremely desirable and acceptable to patients and people in general who are experiencing the types of skin irritation or discomfort, as well as skin care maintenance for normal skin as outlined above.

OBJECTS OF THE INVENTION

It is an object of this invention to provide a refined colloidal oatmeal base, and recreate the beneficial properties in the natural oat seed, using a technique that uses ultra refined particle size of 44 micron colloidal oatmeal into a readily dispersible product for bath, loose powder and cosmetic formulations with all the therapeutic benefits of the oat as described in Federal register official monograph for category 1 skin protectants.

It is another object of this invention to provide a method for formulating a cosmetic binding and thickening agent with emulsification properties to be able to be used in low or high concentrations, is fully functional, one which provides smoothness and elegance to formulations, dry, liquid, lotion or otherwise.

It is a further object of this invention to provide a method for treating skin discomforts as well as maintaining normal skin, in a dry powder, or cosmetic form such as cream, lotion, liniment, ointment and the like, as well as shampoos, conditioners, soaps and bath preparations, sunscreens and the like.

SUMMARY OF THE INVENTION

In accordance with one aspect of the invention, there is provided a composition comprising a carrier, an encapsulation agent, and a binder.

In accordance with another aspect of the invention, there is provided a method for treating a victim of treating skin discomforts as well as maintaining normal skin.

The treatment comprises applying the above-described composition topically to the skin of the victim directly to the area affected to treat skin discomforts as well as maintaining normal skin.

In accordance with a further aspect of the invention, there is provided a method for making a composition useful for topical application to treat skin discomforts as well as to maintain normal skin. The method comprises the steps of: mixing the carrier fluids to form a liquid solution, adding an hydrolyzed agent to distribute the ingredients, and finally adding a encapsulation agent which not only encapsulates the fluid material, but binds it into a powdered form, thus having an ability to evenly distribute the final composition. The resulting dry powder solution preferably has a silky smooth texture which dissolves easily in aqueous or oil phases for liquid, cream, lotion, gel, ointment preparations and the like, as well as having the ability for easy dispersion into dry powder and natural oil formulations.

DETAILED DESCRIPTION OF THE PREFERRED EMBODIMENTS

Colloidal oatmeal is the powder resulting from the grinding and further processing of whole grain oat meeting US standards for number 1 or number 2 oats (7 CFR 810.1001). Constituents are as follows, protein 12%, fat 7.5%, carbohydrate 71%, ASH H2O 9.5%. All oats contain colloids. Colloids are natural materials, which produce a film forming or "barrier" substance on the skin.

There are about 25 varieties of oat cultivated. Avena Sativa is the most common oat. It has a smooth stem, growing up to four feet high, with linear lanceolate, veined rough leaves; loose striate sheaves; stipules lacerate; panicle equal, loose; spikelets pedunculate, pendulous, two flowered, both perfect, lower one mostly awned; paleae cartilaginous, embracing the caryopsis; root fibrous, annual. The grains when separated from their integuments are termed grouts. Oatmeal is ground grain.

Oats contain the following lipid/carbohydrate description; linelic acid 40% and oleic acid 30% (both unsaturated), and palmitic acid 20%, stearic acid 1%, arachidic acid 0.3% (saturated). The typical carbohydrate content (starch) content; amylose 26%, and amylopectin 74%.

Typical amino acid profile (% of amino acids); lysine 4.09%, histidine 2.23%, ammonia 3.28%, arginine 6.72%, aspartic acid 8.47%, threonine 2.86%, serine 3.18%, glutamic acid 23.38%, proline 5.68%, glycerine 5.04%, alanine 4.74%, half cystine 0.54%, valine 6.38%, methionine 1.81%, isoleucine 4.55%, leucine 8.32%, tyrosine 3.25%, phenylalanine 5.52%.

Other constituents include; starch, gluten, albumen protein compounds, sugar, gum oil, and salts.

Colloidal oatmeal and extracts can be obtained from Nurture, Inc, Missoula, Montana and appears as a light biege, dense powder, with no odor.

There are several main constituents of colloidal oatmeal. All constituents are considered usable within the scope of this invention.

The composition of the invention comprises oat protein complex, which comprises colloidal oatmeal as a first active ingredient in range percentages of 0.001 to 98.0 wt %, and hydrolyzed oat protein in powdered form as a second active ingredient in percentage ranges of 0.01 to 50.0 wt %, and another clear liquid active oat extract, oat beta glucan extract, which is extracted from the bran of the oat seed which contains high amounts of oat protein and can be in a base of water, or glycerin, or butylene glycol, or propylene glycol in percentage ranges of 0.01 to 50.0 wt %. The combination of the ingredients form an oat protein complex which is in powdered form. The colloidal oatmeal actually absorbs the hydrolyzed oat protein and liquid active oat bran extract, creating a dry and concentrated powder rich in oat protein and colloidal oatmeal. This powdered form can be used alone, mixed into other dry powder formulations, or added into the oil phase of a cosmetic formulation as a skin protectant. The unique properties of the oat protein complex can be added as a thickener and binder for cosmetic formulations. Because of its unique properties, it is possible to add the colloidal oatmeal in the oat protein complex into formulations at very high percentages not often seen in the industry, as it tends to get too thick. It is another novel feature of the invention that by encapsulating the oat proteins into the colloidal oatmeal that it does not absorb all the water into a working formulation, thereby creating unique emulsions with high quantities of colloidal oatmeal for category 1 monograph claims. The oat protein complex acts as an additive to enhance the treating of skin discomforts as well as maintaining normal skin, and is also unique in its ability to work as a cosmetic binder and thickener which imparts a silky soft feel and matte finish to finished products. The ingredients of the oat protein complex are contained in its own encapsulated carrier base.

Generally speaking, the composition will contain in the range of 0.00125% to 98% by weight of colloidal oatmeal. However, compositions containing less than 100% by weight of colloidal oatmeal will provide a diminished, but still therapeutic, effect. Even trace concentrations of colloidal oatmeal (such as 0.00001% by weight) will provide a minute therapeutic effect. Compositions containing 100% by weight of colloidal oatmeal will also provide a therapeutic effect, except that the increase in hydrolyzed oat protein, active oat extract of beta glucan will not be enhanced by the increase percentage of colloidal oatmeal. The usage range by weight of colloidal oatmeal is broadly encompassed within current FDA guidelines. The present invention increases the amount of hydrolyzed oat protein, active oat extract of beta-glucan that can be used. Generally speaking, a sufficient amount of the at least one second active ingredient is mixed with the carrier fluid to reduce the discomfort of skin irritations and also maintain normal skin.

Preferably, the carrier fluid is deionized, sterile, or purified water, or glycerin, or butylene gylcol, or propelene glycol based and forms an aqueous solution containing the added secondary ingredients. This is preferable for the colloidal oatmeal to act as an encapsulation agent.

Uniquely, in this invention, any or all additional Category 1, 2 or 3 skin protectants can be added as follows; zinc oxide, zinc carbonate and zinc acetate, allantoin, aluminum hydroxide gel, ammonium hydroxide, bismuth subnitrate, boric acid, buffered mixture of cation and anion exchange resins, calamine, cocoa butter, corn starch, dimethicone, ferric chloride, glycerin, kaolin, live yeast cell derivative, petrolatum, polyvinylpyrroildon-vynilacetate polymers, shark liver oil, sodium bicarbonate, sulfur, tannic acid, trolamine, and white petroleum, are considered usable in the scope of the present invention to relieve skin discomforts and maintain normal skin, with active ingredients. Other oat based extracts are also considered to be in the scope of this invention such as, oat flour of all grades, oat starch, oat extract, oatmeal, oat grain and oat grouts.

The novel composition further comprising an encapsulation agent such as colloidal oatmeal, cationic guar derivitives, xanthan gum, gellan gum, topical corn starch, polyvinylpyrroildon-vynilacetate polymers, hydrogenated lecithin, diapotassium glycerizzinate and similar encapsulation agents, or even combinations of these agents, such as colloidal oatmeal, xanthan gum and hydrogenated lecithin; diapotassium glycerizzinate, colloidal oatmeal, and cationic guar derivities to name a few. The colloidal oatmeal has intrinsic SPF, natural sunscreen capability. In addition, the colloidal oatmeal can serve to encapsulate the carrier fluids and binders such as topical starch, gum resins such as; guar gum, gum tragacanth, gum ghatti, gum kanaya and gum arabic, natural cellulose derivatives such as; hyroxyethylcellulose, hydroxypropylcellulose, hydroxymethylcellulose, tamarind gum, tara gum, locust bean gum, psyllium husk powder, pectin, gelatin, aureobusidium pullulans, alcaligens faecalis varmyxogenes, seaweed and other seaweed extracts such as; agar, kappa, inta, carragenan and lambada, triple pressed stearic acid, microcrystalline waxes, and polymeric and polyacrylates to reduce the inflammation effect irritations have on the skin, while still enabling the invention to work effectively on normal skin. Typically, 90.0 wt % colloidal oatmeal is used in this invention, although any amount between 0.20 and up to about 99.0 wt. percent. The colloidal oatmeal works within the scope of this invention because it contains hydrophilic colloids of oats. Other hydrophilic colloids can be derived from wheat, rice, corn, barley, tapioca, potato, maize, shellfish and legumes. These colloids help to provide a protective barrier on the skin to control inflammation. In addition, natural proteins are present in most colloids. Natural proteins are present in the oats in weight percents up to 12.5% of the amino acids in the oats. The invention has found that the colloidal oats enhance, synergistically the protein and amino acid profile of the skin, including the lipid structure, while maintaining a natural 5.6 pH balance.

The hydrolyzed oat protein contains approximately 50.0% protein, 1.0% fat, 15.0% ash, 25.0% carbohydrate (6.5% is beta-glucan), 10.0% moisture. It has a molecular weight of less than 3000 and is substance to skin and hair. It has an extremely high lipid content and is derived from the grout of the avena sativa (which contains 10.0% lipids). The typical amino acid profile (% of amino acids) are as follows; lysine 4.09%, histidine 2.23%, ammonia 3.28%, arginine 6.72%, aspartic acid 8.47%, threonine 2.86%, serine 3.18%, glutamic acid 23.38%, line 5.68%, glycine 5.04%, alanine 4.74%, half cystine 0.54%, valine 6.38%, methionine 1.81%, isoleucine 4.55%, leucine 8.32%, tyrosine 3.25%, and phenylalanine 5.52%. Typically, a range of 0.001%to 10.0% is used as an additive to increase protein content in the complex.

The product is finely ground brown powder with a slightly pungent order. Typically this product can be acquired from Beacon CMP Corp. of Kenilworth, New Jersey.

Oat beta glucan is also available from Beacon CMP Corporation. It is an excellent film former and conditioning additive for skin. In addition, it is used to reduce inflammation on the skin. The unique hydrolyzed oat protein can synergistically react with the oat beta glucan to enhance the effect of the hydrolyzed oat protein to pride enhanced encapsulation of the oat extracts. Additionally, the oat beta glucan is used to reduce irritation and increase the efficacy of the colloidal oatmeal. Typical usage level is 0.001% to 10.0 wt %.

Extracts of avena sativa are usable in the scope of this invention are preferably an extract of avena sativa 1:1 v/v glycerin and water. In the most preferred embodiment, the extract of avena sativa is 10% active within the scope of the present invention. This ester is comprised of avena sativa 1:1 v/v glycerin and water, and is preserved with 0.30 v/v phenoxyethanol. This component is white sparkling clear and has no odor. Typically, 0.1 to 10.0 wt % are typical weight percentages used of this compound in formulations. The active element in this component is the oat extractant, which also acts a carrier fluid to be absorbed and encapsulated into the oat protein complex.

The unique formulation is a topically (externally) applied formulation which has these simultaneous effects, skin protectant, protective barrier, anti-itch, burn relief, inflammation and itching caused by miscellaneous sources, and also have antipruritic effects, by (1) depressing cutaneous sensory receptors to relieve irritation and inflammation (2) creating a normal pH mantle to maintain normal skin, and absorbing irritants from the surface of the skin.

It is the combination of analgesic and skin protectant, which make this invention unique.

It should be noted that other additives may be used in the present invention such as tricalcium phosphate, to prevent each of the disclosed compositions from caking.

In addition, there are several other oat additives, dry and powdered, such as hydrolyzed powders, and liquid forms as well, such various activity levels of oat beta glucan and hydrolyzed oat in bases of; water, propylene glycol, butylene glycol, glycerin, and the like, with or without water that are usable within the scope of this invention.

In addition, there are several other active oat extractives that are usable within the scope of this invention, such as dry and powdered, and liquid forms as well, such as in propylene glycol, butylene glycol, glycerin, and the like, with or without water that are usable within the scope of this invention.

In addition, there are other oat beta glucan additives that may be considered usable within the scope of this invention, in liquid form as well as dry, in bases of propylene glycol, butylene glycol, glycerin, and the like, with or without water that are usable within the scope of this invention derived from sources such as, wheat, maize, corn, rice, legumes, potato, and tapioca. In addition, there are several other grades and refinements of colloidal oatmeal, such as coarse ground, medium grind, fine ground, and powdered that may be considered usable within the scope of this invention. Some oat flours also meet the Federal Register Monograph for category 1, 2, or 3 for skin protectants as well, and are considered to be within the scope of this invention.

Additional components can be added to the formulation, such as "oat flour", and a "oat starch". Oat flour and oat starch is expected to be beneficial in that the also provide colloids, amino acids, lipids, proteins and the like in providing beneficail barrier and protectant type qualities for skin care. In addition, there are oils that can be used within the scope of the formula. Oat oil and oat protein oils are the preferred oil, however several others are contemplated within the formulation such as; mineral oil, white oil, various vegetable and flower oils such as olive, canola, sunflower, wheat germ oil, sesame oil, almond oil, rosehip seed oil, avacado oil, peanut oil, safflower oil, jojoba oil, cocoa butter, apricot seed oil and in combiniations thereof.

Also, for enhancing the composition, other elements may be added to the composition. The following are contemplated:

1. fragrance additives in bases of butylene glycol, propylene glycol, water or oil;
2. topical corn starch, bicarbonate of soda, wheat flour, oat flour, rice starch or zinc oxide;
10 3. wheat proteins, hydrolyzed wheat protein, hydrolyzed rice bran or hydrolyzed corn extract;
4. tricalcium phosphate, to prevent caking;
5. phenoxyethanol, methylparaben, propylparaben and butylparaben, ethylparaben, imadiazodinyl urea or dimethyl dimethyl hydantoin;
6. bicarbonate of soda;
7. calamine;
8. kaolin.

Still others considered usable in the present invention are any and/or all category 1, 2, and 3 skin protectant ingredients listed in the Federal Register such as zinc oxide, zinc carbonate and zinc acetate, allantoin, aluminum hydroxide gel, ammonium hydroxide, bismuth subnitrate, boric acid, buffered mixture of cation and anion exchange resins, calamine, cocoa butter, corn starch, dimethicone, ferric chloride, glycerin, kaolin, live yeast cell derivative, petrolatum, polyvinylpyrroildon-vynilacetate polymers, shark liver oil, sodium bicarbonate, sulfur, tannic acid, trolamine and white petroleum.

A thickening agent, such as xanthum gum, microcrystalline waxes, polymers or guar gum derivatives can be added to the invention to provide a higher density compound.

The present invention is easily dispersed in cosmetic formulations and the like due to its silky smooth powder composition, and its novel feature to not absorb water in the formulation after manufacture to prevent excess thickness and cakiness. It is a natural thickener, emulsifier and binder. The uses of the invention are contemplated for the treatment of irritated, dry and inflamed skin as well for the care and maintenance of normal skin.

In the method of the invention, a victim of irritation or discomfort, as well as application to normal skin, is treated by applying the above-described composition topically to the skin of the victim directly to the area affected by the discomfort or normal application site. The types of irritation or discomfort to which the invention may be applied include those discussed in the background of the invention. Generally speaking, the inventive composition, preferably in ointment or cream form, is applied to the selected area, such as a joint, and rubbed in. The amount applied is not critical. Generally, it should be applied in an amount, which is sufficient to wet the area of application. Usually, the amount used will be in the range of from about 0.3 to about 3.0 ccs. In the form of dry powder, it can also be applied by wetting the dry material with any type liquid directly in the palm of the hand and mixing with the forefinger, then applied as a poultice, cleanser or lotion type preparation and the like.

For the treatment of pruritis or itching, the application of the composition can be repeated as required to control the discomfort. When the preferred composition of the invention is applied, it provides near immediate relief from the itching caused by poison ivy and the like, diaper rash, sunburn discomforts, prickly heat, hives and insect bites, chicken pox, and the like. The relief lasts for several hours. It is surprising that an oat based composition would be useful for the treatment of such discomfort and irritations, as well as maintain normal skin.

For best results in the treatment of skin discomforts and irritations, the treatment should be repeated several times per day, such as in the range of 2 to 8 times per day, preferably 3 to 5 times per day, and continued for several days. Usage levels of 2 to 4 times a day may be used for the maintenance of normal skin, or as desired.

It is contemplated to be within the scope of the present invention to use this formulation for a spray, cream, lotion, gel, foam, ointment preparations, liniments and the like, as well as a loose powder, a bath additive and other bath products such as shampoos and conditioners and an enhanced oil. It is also contemplated to be within the scope of the present invention to use this formulation for sunblock lotion, sunscreen lotion as well as after sun gel. It is further contemplated to be within the scope of this invention to use this formulation in baby wipes and bar soap.

The forgoing is a description of the composition and method of use of an embodiment of the invention. The scope of the invention is considered to include the described embodiment together with others obvious to those skilled in the art.

SUNBLOCK LOTION EXAMPLE

The resulting sunblock lotion composition made in accordance with one embodiment of the invention contains the following ingredients.

| Ingredient | Preferred wt % | Ranges wt % |
| --- | --- | --- |
| colloidal oatmeal | 5.76 | 0.00001 to 50.0 |
| hydrolyzed oat protein | 0.06 | 0.001 to 25.0 |
| oat beta glucan extract | 0.18 | 0.001 to 25.0 |
| benzophenone | 3.00 | 0.01 to 25.0 |
| fragrance | 0.05 | 0.001 to 10.0 |
| cyclomethicone | 2.00 | 0.01 to 25.0 |
| cetyl alcohol | 1.70 | 0.01 to 25.0 |
| propylene glycol | 2.00 | 0.01 to 25.0 |
| dmdm hydantoin | 2.00 | 0.001 to 20.0 |
| isopropyl myristate | 2.00 | 0.01 to 25.0 |
| glyceryl monostearate | 3.00 | 0.01 to 25.0 |
| vitamins A, D & E | 0.50 | 0.01 to 50.0 |
| xanthum gum | 0.50 | 0.001 to 15.0 |
| octyl dodecyl neopantanoate | 11.00 | 0.01 to 30.0 |
| trietholamine | 0.40 | 0.01 to 10.0 |
| oat protein oil | 3.0 | 0.01 to 25.0 |
| water | 62.85 | 0.01 to 75.0 |

Procedure

Phase A; add the preferred amount of propylene glycol into a container. Then add the preferred amounts of xanthan gum, oat protein oil, colloidal oatmeal, hydrolyzed oat protein and oat beta glucan to propylene glycol until dissolved.

Phase B; in a separate container add the glyceryl monosterate, isopropyl alcohol, vitamin A, D and E, octyl dodecyl neopantanoate, benzophenone, cetyl alcohol, fragrance and dmdm hydantoin to cyclomethicone. Then heat this mixture to 40 degrees centigrade. Add phase A to phase B. Maintain the phase A and phase B mixture at 40 degrees centigrade.

Phase C; in a separate container, heat the water to 40 degrees centigrade. Then add phase C to the mixture containing phase A and phase B. Blend this mixture until it is cool and has a uniform consistency.

This formulation is beneficial is that the oat protein complex helps to protect and soothe the skin during hours in the sun. Also, because of the natural intrinsic value of SPF in oats, in some cases lower anounts of benzophenone can be used. The octyl dodecyl neopantanoate also boosts the SPF of the product, making it unnecessary to add methoxycinnamate. This makes a milder sunblock for sensitive skin. The addition of the cyclomethicone also adds waterproof capabilities to the formula.

SUNSCREEN LOTION EXAMPLE

The resulting sunscreen lotion composition made in accordance with one embodiment of the invention contains the following ingredients.

| Ingredient | Preferred wt % | Ranges wt % |
| --- | --- | --- |
| colloidal oatmeal | 5.76 | 0.00001 to 50.0 |
| hydrolyzed oat protein | 0.06 | 0.001 to 25.0 |
| oat beta glucan extract | 0.18 | 0.001 to 25.0 |
| fragrance | 0.05 | 0.001 to 10.0 |
| cyclomethicone | 2.00 | 0.01 to 25.0 |
| cetyl alcohol | 2.00 | 0.01 to 25.0 |
| propylene glycol | 2.00 | 0.01 to 25.0 |
| dmdm hydantoin | 2.00 | 0.01 to 25.0 |
| isopropyl myristate | 2.00 | 0.01 to 25.0 |
| glyceryl monostearate | 5.00 | 0.01 to 30.0 |
| vitamins A, D & E | 0.50 | 0.01 to 25.0 |
| xanthum gum | 0.25 | 0.01 to 15.0 |
| octyl dodecyl neopantanoate | 9.00 | 0.01 to 40.0 |
| trietholamine | 0.40 | 0.001 to 15.0 |
| methoxycinnamte | 1.20 | 0.01 to 25.0 |
| oat protein oil | 3.0 | 0.01 to 50.0 |
| water | 64.60 | 0.01 to 75.0 |

Procedure

Phase A; add the preferred amount of propylene glycol into a container. Then add the preferred amounts of xanthan gum, oat protein oil, colloidal oatmeal, hydrolyzed oat protein and oat beta glucan to propylene glycol until dissolved.

Phase B; in a separate container add, glyceryl monosterate, isopropyl alcohol, vitamin A, D and E, octyl dodecyl neopantanoate, benzophenone, cetyl alcohol, fragrance, methoxycinnamate and dmdm hydantoin to cyclomethicone. Heat this mixture to 40 degrees centigrade. Then add phase A to the heated mixture, and maintain this mixture at 40 degrees centigrade.

Phase C; heat water to 40 degrees centigrade. Then add the heated water to the mixture containing phase A and phase B. Lastly, blend this mixture until it is cool and has a uniform consistency.

This formulation is beneficial is that the oat protein complex helps to protect and soothe the skin during hours in the sun. Also, because of the natural intrinsic value of SPF in oats, in some cases lower anounts of benzophenone can be used. The octyl dodecyl neopantanoate also boosts the SPF of the product. The oat protein complex in the formula also helps reduce irritation form the methoxycinnamate. This makes a milder lotion for sensitive skin. The addition of the cyclomethicone also adds waterproof capabilities to the formula.

AFTER SUN GEL EXAMPLE

The resulting after sun gel composition made in accordance with one embodiment of the invention contains the following ingredients.

| Ingredient | Preferred wt % | Ranges wt % |
| --- | --- | --- |
| colloidal oatmeal | 4.80 | 0.00001 to 50.0 |
| hydrolyzed oat protein | 0.05 | 0.001 to 25.0 |
| oat beta glucan extract | 0.15 | 0.001 to 25.0 |
| dmdm hydantoin | 0.60 | 0.001 to 15.0 |
| glyceryl polymethacralate | 43.9 | 0.01 to 98.0 |
| cyclomethicone | 5.00 | 0.01 to 25.0 |
| fragrance | 0.50 | 0.001 to 10.0 |
| aloe barbadensis gel | 40.0 | 0.01 to 75.0 |
| propylene glycol | 5.00 | 0.01 to 20.0 |
| oat protein oil | 3.0 | 0.01 to 50.0 |

Procedure

In a container add propylene glycol. Then add oat protein oil, colloidal oatmeal, hydrolyzed oat protein, oat beta glucan, fragrance, and cyclomethicone to the the propylene glycol until dissolved. Next add glyceryl polymethacrate and aloe barbadensis gel. Lastly, blend this mixture until it has a uniform consistency. The unique properties of this product are the protective film forming barriers of the oat protein complex. This protective barrier does not allow the aloe barbadensis gel to evaporate off the surface of the skin, thus helping top relieve and repair sun and wind burn discomfort.

What is claimed is:

1. A sunblock lotion composition comprising:

0.00001 wt % to 50.0 wt % colloidal oatmeal;

0.001 wt % to 25.0 wt % hydrolyzed oat protein;

0.001 wt % to 25.0 wt % oat beta glucan extract;

0.01 wt % to 25.0 wt % benzophenone;

0.001 wt % to 10.0 wt % fragrance;

0.01 wt % to 25.0 wt % cyclomethicone;

0.01 wt % to 25.0 wt % cetyl alcohol;

0.01 wt % to 10.0 wt % propylene glycol;

0.001 wt % to 20.0 wt % dmdm hydantoin;

0.01 wt % to 25.0 wt % isopropyl myristate;

0.01 wt % to 25.0 wt % glyceryl monostearate;

0.01 wt % to 50.0 wt % vitamin A;

0.01 wt % to 50.0 wt % vitamin D;

0.01 wt % to 50.0 wt % vitamin E;

0.001 wt % to 15.0 wt % xanthum gum;

0.01 wt % to 30.0 wt % octyl dodecyl neopantanoate;

0.01 wt % to 10.0 wt % trietholamine;

0.01 wt % to 25.0 wt % oat protein oil; and 0.01 wt % to 75.0 wt % water.

2. The sunblock lotion composition of claim 1 consisting of:
- 5.76 wt % colloidal oatmeal;
- 0.06 wt % hydrolyzed oat protein;
- 0.18 wt % oat beta glucan extract;
- 3.00 wt % benzophenone;
- 0.05 wt % fragrance;
- 2.00 wt % cyclomethicone;
- 1.70 wt % cetyl alcohol;
- 2.00 wt % propylene glycol;
- 2.00 wt % dmdm hydantoin;
- 2.00 wt % isopropyl myristate;
- 3.00 wt % glyceryl monostearate;
- 0.50 wt % vitamin A;
- 0.50 wt % vitamin D;
- 0.50 wt % vitamin E;
- 0.50 wt % xanthum gum;
- 11.0 wt % octyl dodecyl neopantanoate;
- 0.40 wt % trietholamine;
- 3.0 wt % oat protein oil; and
- 62.85 wt % water.

3. A sunscreen lotion composition comprising:
- 0.00001 wt % to 50.0 wt % colloidal oatmeal;
- 0.001 wt % to 25.0 wt % hydrolyzed oat protein;
- 0.001 wt % to 25.0 wt % oat beta glucan extract;
- 0.001 wt % to 10.0 wt % fragrance;
- 0.01 wt % to 25.0 wt % cyclomethicone;
- 0.01 wt % to 25.0 wt % cetyl alcohol;
- 0.01 wt % to 25.0 wt % propylene glycol;
- 0.01 wt % to 25.0 wt % dmdm hydantoin;
- 0.01 wt % to 25.0 wt % isopropyl myristate;
- 0.01 wt % to 30.0 wt % glyceryl monostearate;
- 0.01 wt % to 25.0 wt % vitamin A;
- 0.01 wt % to 25.0 wt % vitamin D;
- 0.01 wt % to 25.0 wt % vitamin E;
- 0.01 wt % to 15.0 wt % xanthum gum;
- 0.01 wt % to 40.0 wt % octyl dodecyl neopantanoate;
- 0.001 wt % to 15.0 wt % trietholamine;
- 0.01 wt % to 25.0 wt % methoxycinnamte;
- 0.01 wt % to 50.0 wt % oat protein oil; and
- 0.01 wt % to 75.0 wt % water.

4. A sunscreen lotion composition of claim 3 consisting of:
- 5.76 wt % colloidal oatmeal;
- 0.06 wt % hydrolyzed oat protein;
- 0.18 wt % oat beta glucan extract;
- 0.05 wt % fragrance;
- 2.00 wt % cyclomethicone;
- 2.00 wt % cetyl alcohol;
- 2.00 wt % propylene glycol;
- 2.00 wt % dmdm hydantoin;
- 2.00 wt % isopropyl myristate;
- 5.00 wt % glyceryl monostearate;
- 0.50 wt % vitamin A;
- 0.50 wt % vitamin D;
- 0.50 wt % vitamin E;
- 0.25 wt % xanthum gum;
- 9.00 wt % octyl dodecyl neopantanoate;
- 0.40 wt % trietholamine;
- 1.20 wt % methoxycinnamte;
- 3.0 wt % oat protein oil; and
- 64.60 wt % water.

5. A after sun gel composition comprising:
- 0.00001 wt % to 50.0 wt % colloidal oatmeal;
- 0.001 wt % to 25.0 wt % hydrolyzed oat protein;
- 0.001 wt % to 25.0 wt % oat beta glucan extract;
- 0.001 wt % to 15.0 wt % dmdm hydantoin;
- 0.01 wt % to 98.0 wt % glyceryl polymethacralate;
- 0.01 wt % to 25.0 wt % cyclomethicone;
- 0.001 wt % to 10.0 wt % fragrance;
- 0.01 wt % to 75.0 wt % aloe barbadensis gel;
- 0.01 wt % to 50.0 wt % oat protein oil; and
- 0.01 wt % to 20.0 wt % propylene glycol.

6. The after sun gel composition of claim 5 comprising:
- 4.80 wt % colloidal oatmeal;
- 0.05 wt % hydrolyzed oat protein;
- 0.15 wt % oat beta glucan extract;
- 0.60 wt % dmdm hydantoin;
- 43.9 wt % glyceryl polymethacralate;
- 5.00 wt % cyclomethicone;
- 0.50 wt % fragrance;
- 40.0 wt % aloe barbadensis gel;
- 3.0 wt % oat protein oil; and
- 5.00 wt % propylene glycol.

\* \* \* \* \*